US010993390B2

(12) United States Patent
Krone et al.

(10) Patent No.: US 10,993,390 B2
(45) Date of Patent: May 4, 2021

(54) BREEDING METHODS TO DEVELOP IMPROVED XENIA POLLINATORS

(71) Applicant: Accelerated Ag Technologies, LLC, Ankeny, IA (US)

(72) Inventors: Todd Krone, Johnston, IA (US); Jason Cope, Ankeny, IA (US)

(73) Assignee: Accelerated Ag Technologies, LLC, Ankeny, IA (US)

(*) Notice: Subject to any disclaimer, the term of this patent is extended or adjusted under 35 U.S.C. 154(b) by 167 days.

(21) Appl. No.: 15/934,184

(22) Filed: Mar. 23, 2018

(65) Prior Publication Data
US 2018/0273964 A1 Sep. 27, 2018

Related U.S. Application Data
(60) Provisional application No. 62/476,267, filed on Mar. 24, 2017.

(51) Int. Cl.
A01H 1/02 (2006.01)
C12N 15/82 (2006.01)

(52) U.S. Cl.
CPC ........... A01H 1/02 (2013.01); C12N 15/8216 (2013.01)

(58) Field of Classification Search
CPC ...................................................... A01H 1/02
See application file for complete search history.

(56) References Cited

U.S. PATENT DOCUMENTS

| 4,087,937 | A | 5/1978 | Meador |
| 5,596,838 | A | 1/1997 | Greaves et al. |
| 5,689,914 | A | 11/1997 | Greaves et al. |
| 5,694,700 | A | 12/1997 | Greaves et al. |
| 5,880,331 | A | * 3/1999 | Krebbers ................ A01H 1/02 47/DIG. 1 |
| 6,141,904 | A | 11/2000 | Greaves et al. |
| 6,146,884 | A | 11/2000 | Coonrod et al. |
| 6,865,556 | B2 | 3/2005 | Penner et al. |
| 8,158,850 | B2 | 4/2012 | Feng et al. |
| 8,356,464 | B2 | 1/2013 | Lafargue et al. |
| 8,618,358 | B2 | 12/2013 | Feng et al. |
| 8,943,745 | B2 | 2/2015 | Sexton et al. |
| 9,227,230 | B2 | 1/2016 | Bensley-Bromilow et al. |
| 9,433,161 | B2 | 9/2016 | Cope et al. |
| 2013/0118066 | A1 | 5/2013 | Cope et al. |
| 2013/0118067 | A1 | 5/2013 | Cope et al. |
| 2014/0115730 | A1 | 4/2014 | Cope |
| 2014/0223812 | A1 | 8/2014 | Cope et al. |

FOREIGN PATENT DOCUMENTS

| CA | 966734 | 4/1975 |
| CN | 104145947 | 11/2014 |
| CN | 104957032 | 10/2015 |
| CN | 205926293 | 2/2017 |
| JP | H11192033 | 7/1999 |
| JP | 2009040703 | 2/2009 |
| SU | 1606037 | 11/1990 |
| WO | 2012125593 | 9/2012 |
| WO | 2013070846 | 5/2013 |
| WO | 2014209903 | 12/2014 |
| WO | 2016085355 | 6/2016 |
| WO | 2018129302 | 7/2018 |

OTHER PUBLICATIONS

Murphy et al, Journal of Economic Entomology, vol. 103, No. 1, pp. 147-157 (Year: 2010).*
Webber Xenia, or the immediate effect of pollen, in maize, U.S. Department of Agriculture Division of Vegetable Physiology and Pathology Bulletin No. 22 (Year: 1900).*
Orzolek et al, HortTechnology, vol. 12, No. 3, pp. 461-464 (Year: 2002).*
Urs Weingartner, Olivier Kaeser, Muhua Long, and Peter Stamp: Combining Cytoplasmic Male Sterility and Zenia Increases Grain Yield of Maize Hybrids, Crop Science, pp. 1848-1856 (2002).
Sanford, J.C. and R. E. Hanneman, Jr., The Common Potato Pollen Collector Modified for Bulk Pollen Collection, 1977, News and Reviews.
Bhargava, et al, 1991, An Efficient Potato Pollen Extractor for Bulk Pollen Collection.
Office Action dated Jun. 19, 2018 from U.S. Appl. No. 15/192,519 Covering Grain Production.
Tsai et al, Journal of the Science of Food and Agriculture 57: 163-174, Effects of Cross-pollination on Dry Matter Accumulation, Nutrient Partitioning and Grain Yield of Maize Hybrids Grown under Different Levels of N Fertility, 1991.
Wang et al, 2009, Industrial Crops and Products 29: 182-188, Leaf Photosynthesis is enhanced in normal oil maize pollinated by high oil maize hybrids.
Graybosch et al, 1988, American Journal of Botany 75: 144-156, Male Sterility in soybean—An Overview.
Ortiz-Perez et al, 2007, Field Crops Research 101: 259-268, Insect-mediated cross-pollination in soybean.
International Search Report and Written Opinion of the International Search Authority regarding PCT/US2016/039355 filed on Jun. 24, 2016.
R T Weiland: Cross-Pollination Effects on Maize (Zea mays L.) hybrid yields, CAN, J. Plant Sci, vol. 72, No. 1, Jan. 1, 1992, pp. 27-33.

(Continued)

Primary Examiner — David H Kruse
(74) Attorney, Agent, or Firm — Brick Gentry PC; Brian J Laurenzo; Jessica L. Susie

(57) ABSTRACT

This invention describes a new, high-efficiency method of selecting and advancing pollen donator strains in a breeding or product advancement program, wherein the pollen donator strains are specifically selected to maximize product attributes. Embodiments of this invention relate to the use of a mix of pollen from multiple potential pollen donator strains to cross-pollinate a female corn plant, allowing for single-plant performance comparisons. The comparisons of products from the single plant or less experimental unit allow for the selection of those pollen donator strains that maximize desirable results.

12 Claims, No Drawings

(56) References Cited

OTHER PUBLICATIONS

Cherng-Liang Tsai et al: Effects of cross-pollination on dry matter accumulation, nutrient partitioning and grain yield of maize hybrids grown under different levels of N fertility, Journal of the Science of Food and Agriculture, vol. 57, No. 2, Jan. 1, 1991, pp. 163-174.

J M Shete et al: Study of Heterosis in Top Cross Derivatives of Maize (Zea mays L.), Agric. Sci. Digest, vol. 31, No. 1, Mar. 1, 2011, pp. 1-7.

Want R F et al: Leaf photosynthesis is enhanced in normal oil maize pollinated by high oil maize hybrids, Industrial Crops and Products, Elsevier, NL, vol. 29, No. 1, Jan. 1, 2009, pp. 182-188.

Uribelarrea et al: Enhanced kernel set promoted by synchronous pollination determines a tradeoff between kernel number and kernel weight in temperate maize hybrids, Field Crops Research, Elsevier, Amsterdam, NL, vol. 105, No. 3, Nov. 19, 2007, pp. 172-181.

Carcova Jorgelina et al: Synchronous pollination within and between ears improves kernel set in maize, Crop Science, vol. 40, No. 4, Jul. 2000, pp. 1056-1061.

Barnabas, B. and Rajki, E. (1976). Storage of Maize (Zea mays L.) Pollen at—196° C. in Liquid Nitrogen. Euphytica 25:747-752.

Barnabas, B. (1985). Fertility of deep-frozen maize (Zea mays L.) pollen. Ann. Bot. 48:861-864.

Barnabas B.and Rajki, E. (1981). Effect of water loss on germination ability of maize (Zea mays L.) pollen. Ann. Bot. 55:201-204.

Barnabas, B; Kovacs, G.; Abranyi, A.; and Pfahler, P. (1988). Effects of Pollen Storage by Drying and Deep-Freezing on the Expression of Different Agronomic Traits in Maize (Zea mays L). Kluwer Academic Publishers, Dordrecht—Printed in the Netherlands. Euphytica 39(3):221-225.

Barnabas, B (1994). Preservation of Maize Pollen Biotechnology in Agriculture and Forestry, vol. 25 Maize (ed. by Y. P. S. Bajaj) Springer-Verlag Berlin Heidelberg.

Barnabas, B., and G. Kovacs. (1997). Storage of Pollen. Ch. 14, In: K.R. Shivanna and V. K. Sawhney (eds). Pollen Biotechnology for Crop Production and Improvement. Cambridge University Press.

Basra, A. (1999). Heterosis and Hybrid Seed Production in Agronomic Crops, 81-84.

Collins, T. C.; Lertmongkol, V.; Jones, J. P. (1973). Pollen Storage of Certain Agronomic Species in Liquid Air, Crop Science, 13:493-494.

Connor, Kristina and Towill, Leigh. (1993). Pollen-Handling Protocol and Hydration/Dehydration Characteristics of Pollen for Application to Long-Term Storage, KluwerAcademics Publisher 77-84.

Crevecoeur, M; Clegg, J.S.; Seitz, P.; Seitz, W.; Hazlewood, C.F. (1982). Cellular responses to extreme water loss: the water-replacement hypothesis. Cryobiology 19:306-316.

Crevecoeur, M.; Deltour, R.; Bronchart, R. (1982). Quantitative freeze-fracture study of plasmalemma and nuclear envelope of Zea mays root cells during early germination. J. Ultrastruct. Res. 80:1-11.

Das, S.; Singhal, G.S. (1985). Role of interfacial structured water in membrane: osmotic properties of L-α-Egg lecithin liposomes. J. Membr. Biol. 86:221-227.

Swift, J.G.; Buttrose, M.S. (1972). Freeze-etch studies of protein bodies in wheat scutellum. J. Ultrastruct. Res. 40:378-390.

Virmani, S.S. and M. Llyas Ahmed. (2001). Environment-sensitive genic male sterility (EGMS) in crops. Adv. Agronomy 72: 139-195. DOI: 10.1016/S0065-2113(01)72013-5.

Walden, D. B. (1967). Male Gametophyte of Zea mays L. Crop Science 7:441-443.

Wang, Z; Ge, Y.; Scott, M and Spangenberg, G. (2004). Viability and longevity of pollen from transgenic and non-transgenic tall Fescue (Festuca arundinacea) (Poaceae) Plants. American Journal of Botany 91(4): 523-530.

Webb, M.A.; Arnott, H.J. (1982). Cell wall conformation in dry seeds in relation to the preservation of structural integrity during desiccation. Am. J. Bot. 69:1657-1668.

Pareddy et al. (1989). Production of normal, germinable and viable pollen from in vitro-cultrued maize tassels. Theor Appl. Genet. 77:521-526.

Aylor, Donald E. (2004). Survival of maize (Zea mays) pollen exposed in the atmosphere. Agricultural and Forest Meteorology 123 (2004) 125-133.

Buitink et al. (2000). The effects of moisture and temperature on the ageing kinetics of pollen: interpretation based on cytoplasmic mobility. Plant Cell and Environment (2000) 23, 967-974.

Everett, H.L. (? 1950s?) Studies on Corn Pollen. Thirteenth Hybrid Corn Industry Research Conference.

Kerhoas C. et al. (1987). A multidisciplinary approach to the study of the plasma membrane of Zea mays pollen during controlled dehydration. Plana 171: 1-10.

Nath, J. et al. (1975) Effect of Freezing and Freeze-Drying on the Viability and Storage of Lilium longiflorum L. and Zea mays L. Pollen. Cryobiology 12, 81-88.

Nepi, M. et al. (2001). Pollen hydration status at dispersal: cytophysiological features and strategies. Protoplasma (2001) 216: 171-180.

International Search Report and Written Opinion of the International Searching Authority regarding PCT/US2016/039339 filed on Jun. 24, 2016.

Synchronous Pollination within and between Ears Improves Kernel Set in Maize, Crop Science, vol. 40, No. 4, Jul. 2000, pp. 1056-1061.

Office Action dated Oct. 12, 2018 from U.S. Appl. No. 15/192,485 Covering Seed Production.

Communication pursuant to Article 94(3) EPC regarding European Patent Application No. 16 739 302.4 dated Feb. 12, 2019 Covering Seed Production.

Communication pursuant to Article 94(3) EPC regarding European Patent Application No. 16 738 296.9 dated Feb. 18, 2019 Covering Grain Production.

Communication pursuant to Rules 161(1) and 162 EPC regarding European Patent Application No. 17 718 712.7 dated Feb. 12, 2019 Covering Pollen Field Conditioning and Preservation Method.

Koga, Y., et al. (1971). Studies on the longevity of pollen grains of rice, Oriza sativa L. 1. Morphological change of pollen grains after shedding. Cytologia 36: 104-110.

Mouradian, R.; Womersley, C.; Crowe, L.M.; Crowe, J.H. (1985). Degradation of functional integrity during long-term storage of a freeze-dried biological membrane. Cryobiology 22:119-127.

Nirmala, B., et al. (2009). Economics of hybrid rice seed production in India. p. 495-503. In: F. Xie and B. Hardy (eds) Accelerating Hybrid Rice Development. Intl Rice Research Institute.

Pfahler, P. L.; Linskens, H. F. (1972). In vitro germination and pollen tube growth of maize (Zea mays 42:136-140. L.) pollen Theoretical and Applied Genetics.

Platt-Aloia, K.A.; Lord, E.M.; de Mason, D.A.; Thompon, W.W. (1986). Freeze fracture observations on membranes of dry and hydrated pollen from Colomia, Phoenix and Zea. Planta 168:291-298.

Platt-Aloia, K.A.; Thomson, W.W. (1985). Freeze-fracture evidence of gel-phase lipid in membranes of senescing cowpea cotyledons. Planta 163:360-369.

Priestley, D.A.; De Kruijff, B. (1982). Phospholipid motional characteristics in a dry biological system. A 31P nuclear magnetic resonance study of hydrating Typha latifolia pollen. Plant Physiol. 70:1075-1078.

Priestley, D.A.; Werner, B.G.; Leopold, A.C.; McBride, M.B. (1985). Organic free radical levels in seeds and pollen: the effects of hydration and aging. Physiol. Plant. 64:88-94.

Senaratna, T.; McKersie, B.D.; Stinson, R.H. (1985). Simulation of dehydration injury to membranes from soybean axes by free radicals. Plant Physiol. 77:472-474.

Song, Z.P., et al. (2001). A study of pollen viability and longevity in Oryza rufipogon, O. sativa, and their hybrids. p. 31-32. IRRI Pub. 26.2.

Southworth, D.; Branton, D. (1971). Freeze-etched pollen walls of Artemisia pycnocephala and Lolium humboldtii. J. Cell Sci. 9:193-207.

United States Office Action U.S. Appl. No. 15/192,485 Covering Seed Production dated Jan. 22, 2018.

(56) References Cited

OTHER PUBLICATIONS

Notification Concerning Transmittal of International Preliminary Report on Patentability and International Preliminary Report on Patentability from PCT/US2016/039339.
Notification Concerning Transmittal of International Preliminary Report on Patentability and International Preliminary Report on Patentability from PCT/US2016/039355.
Office Action dated Apr. 12, 2019 from U.S. Appl. No. 15/486,737 Covering Pollen Field Conditioning and Preservation Method.
Ishikawa, M. Kitashima, T., Hemachandra, P.V., Yamaguchi, E. and Toyomasu, T. (2005), Seed Sci. & Technol., 33, 7541-752 Constant relative humidity chgambers using phosphoric acid for controlled desiccation of small recalcitrant.
International Search Report and Written Opinion of the International Searching Authority from PCT/US2017/027381.
Cicero Almeida et al: Conservation and in vitro germination of pollen of maize, Brazilian Journal of Botany, vol. 34, Oct. 1, 2011, pp. 493-497.
Connor Kristina F et al: Pollen-handling protocol and hydration/dehydration characteristics of pollen for application to long-term storage, Euphytica, vol. 68, No. 1-2, 1993, pp. 77-84.
Forsberg R A et al: Sources, Maintenance, and Utilization of Parental Material, Jan. 1, 1980 (Jan. 1, 1980), hybridization of crop plants, American Society of Agronomy, Inc.: Crop Science Society of America, Madison, WI, pp. 65-81.
N. Sukhvibul et al: Medium and long term storage of Anigozanthos manglesii (D. Don) pollen, New Zealand Journal of Crop and Horticultural Science, vol. 21, No. 4, Dec. 1, 1993 (Dec. 1, 1993), pp. 343-347.
Barnabas B et al: Adhesion and Germination of Differently Treated Maize Pollen Grains on the Stigma, ACTA Botanica Hungarica, vol. 30, No. 3-4, 1984, pp. 329-332.
Office Action dated Apr. 30, 2018 from U.S. Appl. No. 15/486,737 Covering Pollen Field Conditioning and Preservation Method.
Almeida et al (Brazilian Journal of Botany (2011), Conservacao e germinacao in vitro de polen de milho, vol. 34 (4), pp. 493-497.
Volk, Gayle (2011) Collecting Pollen for Genetic Resources Conservation. Ch. 25.
Connor, Kristina F. (1993) Pollen-Handling protocol and hydration/dehydration characteristics of pollen for application to long-term storage.
Office Action dated Feb. 9, 2018 from U.S. Appl. No. 15/192,519 Covering Grain Production.
Dickinson, H.G.; Elleman, C.J. (1985). Structural changes in the pollen grain of *Brassica oleracea* during dehydration in the anther and development on the stigma as revealed by anhydrous fixation techniques. Micron Micros. Acta 16:255-270.
Elleman, C.J.; Dickinson, H.G. (1986). Pollen stigma interactions in Brassica. IV. Structural reorganisation in the pollen grains during hydration. J. Cell Sci. 80:141-157.
Ganeshan, S., et al. (2008). Cryopreservation of Pollen. Ch. 17, In: B.M. Reed (ed), Plant Crypreservation: A Practical Guide. Springer.
Heslop-Harrison, J. (1979). An interpretation of the hydrodynamics of pollen. Amer. J. Bot. 66: 737-743.
Heslop-Harrison, J.; Heslop-Hanison, Y. (1985). Germination of stress tolerant Eucalyptus pollen. J. Cell Sci. 73:135-157.
Hoekstra, F.A., and J. Bruinsma. (1975). Respiration and vitality of binucleate and trinucleate pollen. Physiol. Plant. 34: 221-225.
Kaku, S.; Iwayainove, M.; Gusta, L.V. (1984). Relationship of nuclear magnetic resonance relaxation time to water content and cold hardiness in flower buds of evergreen azalea. Plant Cell Physiol. 25:75-882.
Khatum, S., and T.J. Flowers. (1995). The estimation of pollen viability in rice. J. Exp. Bot. 46:151-154.
King, J.R. (1965). The storage of pollen—particularly by the freeze drying method. Bull. Torrey Bot. Soc. 92: 270-287.
Körnicke, FR.; Vorläufige Mittheilungen über den Mais; 1872; Bonn, Germany.
English Translation of Körnicke, FR.; Vorläufige Mittheilungen über den Mais (Preliminary Information on Corn); 1872; Bonn, Germany.
Ford, Rosemary H.; Inheritance of Kernel Color in Corn: Explanations and Investigations; The American Biology Teacher; Mar. 2000; pp. 181-188; vol. 62, No. 3; Chestertown, MD.

* cited by examiner

BREEDING METHODS TO DEVELOP IMPROVED XENIA POLLINATORS

CROSS REFERENCE TO RELATED APPLICATIONS

This application claims priority to U.S. Provisional Patent Application No. 62/476,267 filed Mar. 24, 2017 and titled BREEDING METHODS TO DEVELOP IMPROVED XENIA POLLINATORS. The entire contents of U.S. Provisional Patent Application No. 62/476,267 are hereby incorporated by reference.

FIELD OF THE INVENTION

This invention relates generally to a novel high-efficiency method of conducting a yield trial to select and advance pollen donor strains, wherein the pollen donor strains are specifically being tested for their ability to increase maize grain yields or other desirable product attributes, and being selected for further trials or use in commercial pollination programs. More specifically, this invention relates to the use of a mix of pollen from multiple potential pollen donor strains to cross-pollinate a female corn plant, allowing for single-ear performance comparisons or comparisons with a small number of ears.

BACKGROUND

The current invention has application to the field grain yield trials, usually conducted for the purpose of breeding and product advancement. In one embodiment, the invention is applicable to maize (corn) yield trials. The trials may be conducted to analyze other plant product attributes in addition to yield. The term "breeding and product advancement" is used herein to mean the practice of improving the genetic potential and resulting yield of a crop, which may also include improvement of other crop attributes. A field used for the purposes of breeding and product advancement is generally referred to as a research test plot, a product development test plot, or a pollinator test plot. The term "high efficiency" is used herein to mean a statistically significant, measurable improvement over existing known methods in terms of resource utilization (i.e., land and labor) and total number of plants required to make an informed decision regarding yield benefit or other crop attribute benefits. The term "pollen donor strain" is used herein to mean a strain being used as a pollen donor for pollinating another strain of the same species. A pollen donor strain is a strain whose pollen is intended to be collected, and optionally conditioned and/or preserved and stored, prior to being used to make pollinations on female plants. With respect to maize, this contrasts with a conventional system in which corn plants are allowed to self-pollinate, or in which pollen from a second corn strain is planted alongside the first strain, such that the second strain acts as the pollinator for the first. The pollen donor strains of interest are those which have shown greater yield benefits or other benefits in comparison with other pollen donor strains on that female in previous studies. In the context of this disclosure, a pollen donor strain is being tested for its ability to increase grain yields and other desirable product characteristics. The yield may be increased as a result of using that strain as the sole pollen donor for a grain production field, or using the inbred in conjunction with one or more other inbreds as pollen donors for a grain production field. The indefinite articles "a" or "an" carry the meaning of "one or more" in the context of this disclosure.

For the purposes of this disclosure and its applicability to breeding and product advancement, the term "self-pollen," which is a single plant's own pollen, includes "sib-pollen," which is pollen from genetically identical plants. Likewise, the term "self-pollination" includes "sib-pollination," which is pollination occurring with pollen from a sibling plant, and which has the same effect in the resulting grain as self-pollination. For this disclosure, the term "selfing" means pollination either by self-pollination or sib-pollination, both being variants of pollination of plants who share the same genetics. "Cross pollination," for the purposes of this disclosure, refers to genetic exchange resulting from pollen produced by another genetically distinct plant. Thus, cross pollination is the introduction of pollen that is derived or sourced from separate plants that are genetically distinct from the pollen which will be shed from the plants within the field or alternate growth environment.

At present, seed companies do not purposefully select and advance pollen donor strains for the primary purpose of using them as a source of pollen to be collected in large quantities, conditioned or preserved, and then used to pollinate plants in a different location. Rather, seed companies currently test and advance strains for the ability of the progeny seed to generate yield, high oil, or other desirable traits exclusively in a field-based setting where those pollinator plants act as pollinators to neighboring plants. In current practices, the breeding and advancement of strains is reliant upon self-pollination rather than cross-pollination, so the testing and advancement of pollen donor strains has not been previously practiced. The disclosed invention uses the testing and advancement of pollen donor strains to create an index of specific pollen strains that provide the greatest improvement in yield and other desirable agronomic traits when used as source to pollinate female plants of known genetic background. Further, on the breeding products, such as grain, different strains are distinguishable from one another based on differences in either visual or internally detectable seed characteristics.

In 1881, botanist Wilhelm Focke coined the term "xenia" to refer to the effects of pollen on maternal tissues in a plant. At the time, the endosperm was thought to be maternal tissue. Over time, the term "xenia" or "xenia effect" has been used to describe the effect of pollen genes on the seeds and fruit of a fertilized plant, which includes effects on the endosperm (Bulant et al. ((2000) *Crop Sci.* 40: 182-188). The present disclosure takes advantage of the xenia effect by using it to establish differences in product attributes from different sources of pollen. In some embodiments, the invention may be used to identify improved product attributes.

"Product attributes," for the purpose of this disclosure, are measurable characteristics of breeding products. In one example, product attributes may be measurable characteristics of a maize kernel. Kernel attributes may include, but are not limited to, oil content, protein content, starch content, kernel weight, test weight, kernel size, kernel color and a variety of biochemical measurements that can be made on the kernel, such as amino acid levels, tocopherol levels, levels of various nutrients, micro-nutrients, vitamins, flavonoids, and other compounds. Products include, but are not limited to, seed, grain, fruit, and other ovarian tissues that result from plant breeding.

Numerous studies have shown the breadth and diversity of the xenia effect with respect to maize—that is, the influence of the pollen source on the development of the kernel. Among the earliest demonstrations (Kiesselbach, T.

A. (1926) *Neb. Agric. Exp. Stn. Bull.* 33:1-69; Kiesselbach, T. A. & W. H. Leonard (1932) *J. Am. Soc. Agron.* 24:517-523), Kiesselbach reported that relative to self-fertilization, cross fertilization increased kernel weights on average by 10.1% (11.8% for embryos, 10.4% for endosperm, and 3.2% for pericarp). Tsai and Tsai (Tsai, C. L. & C. Y. Tsai (1990) *Crop Sci.* 30: 804-808) showed an increase in grain yield of about 30% and in increase in kernel protein content of about 44% in an early hybrid when it was pollinated by a late hybrid. Using maize inbred lines with normal endosperm, Bulant et al. ((2000) *Crop Sci.* 40: 182-188) reported a relative advantage in weight of cross-fertilized to self-fertilized kernels as great as 13%. Breeding studies at South Dakota State University confirm that cross pollination of specific hybrids can increase kernel size and protein content, and that cross pollination between hybrids of similar maturity accounts for 40 to 60% of kernels formed in mixed stands (Wicks III, Z., (1994) *Proc. Annual Corn and Sorghum Res. Conf.* 4.

The development of kernels can be altered by cross pollination (Tsai, C. L. & C. Y. Tsai (1990) *Crop Sci.* 30: 804-808; Poneliet, C. G. and D. B. Egli, (1983) *Crop Sci.* 23:872-875). Poneliet and Egli (1983) showed that the duration of the effective filling period from cross-fertilization often was greater than that from self-fertilization. Pollen source also affects endosperm development in terms of protein content, amino acid profile, and translucency. (Pixley, K. V. and M. S. Bjarnason (1994) *Crop Sci.* 34:404-408; Bulant et al. (2000) *Crop Sci.* 40: 182-188). At 14 days after pollination, the advantage of cross-fertilization on average was 28.8% for starch content, 24.8% for ADP-glucose-pyrophosphorylase (EC 2.7.7.27) activity, and 24.1% for neutral invertase (EC 3.2.1.26) activity (Bulant et al. (2000) *Crop Sci.* 40: 182-188). Tsai et al. ((1991) *J. Sci. Food Agric.* 57: 163-174) modified P3732 endosperm through cross-pollination, which significantly increased kernel weight, kernel protein content and grain yield across a range of fertilizer N treatments. The additional nutrients translocated into developing kernels of P3732 cross-pollinated plants were mainly derived from increases in duration of dry matter production and N uptake by vegetative tissues (Tsai et al. (1991) *J. Sci. Food Agric.* 57: 163-174). These well-established impacts on kernel composition are the basis for the top-cross method of producing high oil corn.

The top-cross system for high oil corn grain production was a method used in the 1990s and early 2000s in which high oil was induced by planting a blend of a male sterile hybrid (~93%) and a male fertile high oil pollinator germplasm (7%). The result was an increase in oil from about 3-4% for normal commodity grain, to about 6% for the high oil top-cross grain. The high oil grain brought a premium price per bushel at the grain elevator. (Thomison, P. R. et al. (2002) *Agron. J.* 94: 290-299) A new pollinator would be derived from these crosses, but the plot size was very large in order to maintain a level of minimum purity in the middle of the plot from which the oil and yield data was being collected.

The extent of the xenia effect varies with the male and female genotype. The greater the genetic difference between the male pollen source and female, the greater the expected response to cross-pollination. (Leng, E. R., (1949) *Agron. J.* 41:555-558; Bulant, C. and A. Gallais, (1998) *Crop Sci.* 38: 1517-1525). The cross-fertilization advantage was less for single-cross hybrids than for their inbred parents, and the advantage varies with the male. For crosses between inbreds, the advantage of cross fertilization was 13.8 and 14.5%, but only 2.5% for crosses made with their hybrid (Bulant, C. and A. Gallais, (1998) *Crop Sci.* 38: 1517-1525). Both pollen and maternal effects impact the response to cross pollination (Seka, D and H. Z. Cross (1995) *Crop Sci.* 35: 80-85; Seka, D. et al. (1995) *Crop Sci.* 35: 74-79).

Results of cross pollinations between hybrids observed by Bulant and Gallais (Bulant, C. and A. Gallais, (1998) *Crop Sci.* 38: 1517-1525) illustrate that cross fertilization can increase the sink strength of the whole ear and that the kernel mass benefit can be observed under unfavorable conditions. The positive xenia effects have been interpreted in terms of source-sink relationships. If the resources are limiting, the increase in sink strength leads to a greater average kernel weight with mixed fertilization than with pure self-fertilization. There was no relationship between the cross-fertilization advantage and the average seed weight of the self-fertilized female or male pollen source. Cross-fertilization advantage was beneficial for small kernels as well as for large kernels (Bulant, C. and A. Gallais, (1998) *Crop Sci.* 38: 1517-1525).

Given that the intent of cross pollination is typically to increase yield and improve product characteristics, the varieties that are selected for use in cross-pollination generally both display desirable characteristics that would be expressed in the resulting product. In the case of maize, a pollinator would typically be chosen that resulted in high yield and high starch content in the pollinated kernels.

Pollination success is critical to grain yield. Grain yield is measured as the weight of grain per area of land measured at a given moisture content (for example, 15.5% moisture for corn). Low pollination rates result in poor grain yield. For this reason, grain producers typically rely upon self-pollination and pollination by neighboring plants in the field since they know that the pollination will occur during the correct window of time because the female components of the plant will be ready to receive the pollen. Unfortunately, self-pollination results in inbreeding depression which negatively impacts grain yield (Scheffler et al. (2008) *Maydica* 53: 189-198) and it is unable to account for changing conditions and stresses that may affect the plant during the growing season.

Given recent advancements in the field of pollen conditioning and preservation (as provided in US20170238535, the entire contents of which are hereby incorporated by reference) and the use of intentional pollination using collected and optionally preserved pollen (as provided in US20160374279 and US20160374280, the entire contents of which are hereby incorporated by reference) for seed and grain production, the ability of using pollen donor strains for the purposes of expressly pollinating field-grown crops has become a feasible production method. The pollen donator strains used in such activities can be carefully characterized and selected based on their ability to maximize grain yield or other desirable product desirable attributes respective to the pollen donators used with a designated female. From this information, a comprehensive database can be assembled for use in selecting a given male pollen donator to bring out the maximum yield response or other desirable responses from a designated female.

Accordingly, there is a need in the industry for an invention which allows for the improvement of efficiency in the selection and advancement of high-yielding pollen donator strains. There is also a need in the industry which allows differences in yield or other desirable product characteristics to be tested all on a single plant, reducing variation caused from plant to plant comparisons and reducing the amount of labour, land and other resources required to conduct conventional plot yield trials. Finally, there is a need in the industry for choices of pollen that can be used to intentionally pollinate a field of crops to provide the highest yield or other desirable product characteristics under a given set of challenging field conditions.

SUMMARY OF THE INVENTION

Provided is a method of plant breeding comprising, growing a designated female plant; pollinating said designated female plant with at least two types of pollen selected from the group consisting of: a first male pollen donor strain wherein pollination occurs via intentional pollination resulting in a first cross-pollinated product, a second male pollen donor strain wherein pollination occurs via intentional pollination resulting in a second cross-pollinated product, self-pollen wherein pollination occurs via intentional pollination to produce self-pollinated product, and self-pollen wherein pollination occurs via natural pollination to produce self-pollinated product, wherein said products have distinguishable phenotypes; growing the designated female plant to maturity; harvesting the products; sorting the products from each other based on said distinguishable phenotypes; and comparing product attributes of the products. The product attributes of said products may then be compared, such as for product advancement, or for validating, selecting, storing and applying a pollen donor source which, when applied to a designated female plant in a grain field, will enable the maximum yield response or other desirable characteristics response predicted by earlier rounds of testing.

The at least two types of pollen may include pollen from a first male pollen donor strain and self-pollen. Furthermore, the at least two types of pollen may include pollen from first and second pollen donor strains. In addition, the at least two types of pollen may include pollen from first and second pollen donor strains and self-pollen. Moreover, the at least two types of pollen may include pollen from 1, 2, 3, 4, 5, 6, 7, 8, 9, 10, 11, 12, 13, 14, 15, 16, 17, 18, 19, or 20 male pollen donor strains.

In another embodiment, the plurality of designated female plants is grown in specific challenging field conditions selected to allow the identification of designated male pollen donor strains that provide the highest yield under said challenging field conditions. In other embodiments, the distinguishable phenotypes may be caused by a genetic modification, such as a transgene. In some embodiments, the plant may be corn, wheat, rice, sorghum, oats, or barley.

DETAILED DESCRIPTION

The following is a detailed description of an embodiment of technology and a method enabling an improved method of selecting pollen donor strains for further breeding and product advancement. Such methods may be useful in grain production. The primary goal of selecting a pollen donor for the purpose of grain production is the resulting harvest of a high-yielding, high quality grain. A secondary goal in selecting a pollen donor for the purpose of grain production is to maximize grain harvest when growing conditions are particularly challenging or when market demand indicates that the grain resulting from pollinations using a different pollen donor, rather than self-pollinations, would be beneficial. Finally, in situations where a grain field is at risk to have all of the pollen shed occur prior to the emergence of the pollen receptors, the resulting pollinations using a different donor than self-pollinations would recover a total loss in grain production.

As discussed above, the current invention is applicable to the practice of seed and grain research programs in which pollen donor strains are routinely tested and assessed for advancement in breeding and product advancement programs. This invention provides an improved alternative by modifying the experimental unit from a whole row or plot of plants to a single plant, less than a single plant, or a few plants, thereby significantly reducing the resources needed to achieve the same result. In addition, this method reduces statistical error by increasing replication and precision, while eliminating plant-to-plant variations which occur in the single pollinator source methods currently used. While this disclosure outlines the invention primarily with respect to maize, it is understood that this invention can be applied to other crops producing a seed-bearing structure that allows for the production of multiple seeds wherein the seeds can be compared to each other using visual characteristics or other defining characteristics that allow differentiation between seeds resulting from self-pollination versus those resulting from cross-pollination. Examples of such crops include wheat, rice, sorghum, oats, barley and other cereal crops.

Use of the term "intentional" with regard to pollen application means the specific application of pollen in a way that does not include natural pollination by wind, insect activity or other naturally-occurring conditions. Intentionally applied pollen is pollen that has been applied to a plant as a result of a deliberate human activity or decision, and may be applied by hand or by other means.

For the purpose of this invention, pollinations would typically be conducted by hand, but can also be conducted by mechanical means. The pollinations would typically be conducted by hand because for the invention, the selection process can use just a single plant, or a small number of ovaries less than that found on an entire plant, in order to choose pollen donor strains for advancement. Thus, only a small number of plants need to be pollinated. Pollen delivery methods include, but are not limited to, manual delivery, manual delivery with a small hand mechanical device for semi-automated dispersal, by field driven machinery containing pollen dispersal machinery or via fully automated dispersal by a self-propelled and/or human guided apparatus such as a drone that has a pollen dispersal device mounted to it, wherein the pollen dispersal is by automatic or semi-automatic means, including, but not limited to, positive pressure, negative pressure, mechanical or pneumatic means.

Delivery of the male pollen is intentional, can occur as soon as females are receptive, and preferably excludes non-intentional self-pollination. Any method may be used to exclude non-intentional self-pollination. In some embodiments, delivery of pollen may occur prior to the designated female shedding pollen on any given day, thus enabling a successful cross pollination with all receptive females. In other words, the female component of the plant is open to receive pollen from a male before the male component of the same plant is ready to produce pollen. This method may be used in corn, for example, where females are receptive to pollen when the silks are exposed to receive the pollen. The silks are receptive to pollen prior to emergence and remain receptive for many days after emerging from the husks. Moreover, in corn, two possibilities exist: pollen may be shed prior to silk emergence (protandry), or silk emergence may be prior to pollen shed (protogyny). In either case, the silks will be receptive to pollen before pollen is shed on a given day. This invention may be practiced in both situations. Moreover, in some examples, the silks are receptive to pollen all day for about seven days. Accordingly, pollen may be intentionally applied any number of times, including but not limited to, once per day, twice per day, or in a continuous application. In other embodiments, exclusion of non-intentional self-pollination may occur through male sterility. For example, in corn, designated female plants may be detasseled before intentional pollination. In other embodiments, chemical or genetic male sterility may be used. Male sterility may also be preferable in plants where pollination occurs before the flower is open to receive pollen, such as in soy, wheat, and rice. Moreover, the flower may be manipulated to receive pollen before self-pollen is available. Such manipulation may be genetic, mechanical, chemical, physical, or other.

The pollen used in the present invention can be a single strain of pollen, or it can be a mix of different pollens. Pollination may be conducted by means of shoot bagging or other typical methods known in the art. The mix of individual strains of pollen included may be 1, 2, 3, 4, 5, 6, 7, 8, 9, 10 or more strains of pollen donator pollen. The experimental unit may be as small as single plant. The pollen donator strains used in the mix preferably all have different genetic backgrounds and therefore preferably result in differentiated kernels on the ear. The pollen can be freshly collected pollen, or it can be pollen that has been collected, optionally subjected to field conditioning practices, and stored in such a manner to retain the viability of the collected pollen for later use. The donator pollen can be applied as a mixture or can be applied to the pollen receptors on a single plant one source at a time.

In order to ensure that the product pollinated by each of the one or more different candidate pollen donator strains can be identified, different phenotypic markers should be used in each strain. This will allow the separation of the grain into groups defined by their pollen donator strain. For example, employing a genetic marker in the male parent line that is transmitted in the male pollen and expressed in the resulting product as a distinct and distinguishable phenotype would allow for sorting of this nature. The genetic marker may confer a phenotype that is distinguishable on the basis of seed color, seed color intensity or pattern, seed shape, seed size, seed density, or other seed characteristics. A seed company could employ their own specific marker as distinct from other companies, such as distinct native seed traits or genetically modified color markers that would potentially be invisible to the naked eye. The seeds may then be visually or mechanically sorted based on the marker phenotype. See, for example, Raboy et al. (2000) *Plant Physiol.* 124: 355-368; Evans, M. M. S. & Kermicle, J. L. (2001) *Genetics* 159: 303-315; Jenkins, M. T. (1925) *J. Heredity* 16: 307-310; and Chase, S. (1949) *Genetics* 34: 328-332). For some crops in developing nations where labor is very inexpensive, this sorting could be done manually, while in other situations it would be more economical to have an automated or semi-automated seed sorter such as a Satake Seed Sorter, for example, or an optical scanning system capable of scanning and sorting the seeds. Such a marker may be currently known or may be developed in the future without departing from the scope of this invention.

In some embodiments, examples of markers that can be used in maize include, but are not limited to, white/yellow endosperm, yellow/orange endosperm, opaque/normal endosperm, normal/purple plumule, colorless/purple aleurone, starch endosperm mutants, or any combination of these markers and other maize markers. Non-crop specific transgenic markers include, but are not limited to, color marker genes (such as DsRed2) or any transgene that alters any normal seed phenotype, such as transgenes that increase anthocyanin or other pigments in a seed part or transgenes that alter the color of cotyledons.

The acquisition of male pollen required to make seeds that will mature into product can be via a pollen bank. A pollen bank is a source of stored pollen that has been collected from one or more pollen sources and stored in such a way that the pollen retains its viability. The plants that have been used as the pollen source for such a pollen bank may have been grown and harvested in any conditions, including but not limited to, a field, a growth chamber, a greenhouse, a glasshouse, a shade house, a hoop house, a vertical farming facility or a hydroponic facility. Pollen from a pollen bank may have been sourced in different ways. For example, in one embodiment, fresh pollen can be harvested from males grown in a controlled environment in which the circadian rhythm is 2-8 hours ahead of naturally growing female plants in the field. This method will be further detailed below. In another embodiment, the pollen which is stored in the bank may be preserved pollen that was collected days, weeks, months or years prior to its eventual removal from the bank for pollinating purposes. Preserved pollen may have been preserved by any means that permits the pollen to retain viability, including but not limited to various forms of cooling or freezing including, but not limited to, chilling, cryopreservation, freeze drying, or storage in liquid nitrogen.

In one or more embodiments, the pollen may be harvested from an anther studio. The anther studio enables optimal growth conditions for male plant reproductive tissues for any species or variety of plant. The tissues (corn tassels for example) are cut from plants growing in standard outdoor conditions, such as in the field or those grown in controlled conditions, such as the greenhouse or a growth chamber. The tissues are preferably cut prior to the plant beginning to shed pollen and are placed into the anther studio. The tissue may then be cultured in a nutrient medium allowing for further growth. At least one of specialized lighting, temperature, and/or humidity may be cycled in the anther studio, allowing for continued growth of the tissue. Growth may be modulated to increase or slow the rate of growth and thus modulate the duration for availability of pollen. This enables the ability to have on demand pollen for pollinations that can be accomplished at any time of the day or night. This has utility for pollination enablement of several beneficial and valuable processes related to seed and grain production. It also provides concentrated sources of pollen for preservation purposes. Any pollen harvested from the anther studio and preserved could be utilized in the same manner as the freshly harvested pollen, but at a duration long after the fresh pollen, which has not been preserved, has died. Finally, an anther studio may be scaled to produce relatively large volumes of pollen which are adequate for seed production or grain production level processes. (R. I. Greyson (1994) Maize inflorescence culture. p. 712-714. In: M. Freeling, V. Walbot (eds), The Maize Handbook; Springer-Verlag, New York; J. B. Schoper, R. J. Lamber, B. L. Vasilas, and M. E. Westgate (1987) *Plant Physiol.* 83: 121-125)

This invention can be practiced in any environment including, but not limited to, ideal or target growing environments, off-season environments, or controlled environments (e.g. shade/glass/green/hoop houses, growth chambers, vertical farming facilities, hydroponic facilities, aeroponic facilities etc.).

One advantage of using the disclosed invention is the ability to select specific pollen donator strains for advancement and breeding with the goal of using them in situations with challenging field conditions. For example, many fields present challenges to growers due to higher or lower than optimal soil moisture conditions resulting in annual problems with flooding or drought. The disclosed invention allows seed companies to develop pollen donator strains that are specifically bred for these conditions, and that will provide pollen-delivered traits to improve grain yield in the non-optimal soil moisture conditions. Testing pollen donator strains in variable soil moisture conditions to determine their effect on yield can be easily conducted using the method of the present invention. Those strains that result in higher yields despite the challenging conditions will be advanced to further breeding trials and the best performers will be chosen for commercialization as pollen donator strains for pollinating crops that are facing challenging field conditions of a specific nature. This will allow for the development of a library of pollen donator strains from which growers can choose ideal pollen for their particular conditions or for particular market situations.

This same process can be applied to address a wide range of production conditions commonly faced by grain producers. Conditions that can be addressed by the selection and advancement of specific pollen donator strains include: higher or lower than optimal temperatures, higher or lower than optimal soil pH, shorter or longer growing seasons, and high insect or disease pressures (in particular, ear pests and diseases). In addition, the disclosed invention can be used across a range of fertility conditions. For example, in a field with low fertility, which may be a result of a range of variables, such as different micronutrient levels, a pollinator can be selected to improve yield despite the low fertility. In cases where a field has high fertility which changes over the growing season as a result of challenging conditions, a pollen donator can be used that is specifically characterized to improve grain yield in such conditions, thereby restoring any fertility losses.

The efficiencies of the disclosed invention can be described with respect to maize by comparing the invention carried out with maize to the high oil topcross (HOTC) program mentioned earlier in this specification. As discussed, the HOTC program used included a high-oil pollinator (7% of the plants) with a high-yielding, male-sterile hybrid (93% of the plants) to provide a higher oil grain end product. Table 1, below compares the HOTC system with the invention. The invention has significant gains as a result of much smaller plot size, far less labour, and the ability to test more pollinators.

a single plant with 1-2 ears of corn (very uniform conditions among the kernels on the ears and no plant to plant variation confounding the data) rather than a plot that is much larger consisting of many plants.

Following the use of the pollen donator strains to be tested, the product is collected from the mature female plant ovaries, such as an ear of corn or other fruit, and separated into groups based upon the pollination results—self pollinations being one group, and then one or more groups of product from the cross-pollinations depending upon the number of pollen donator strains being tested. For each group of product, the overall yield increase or decrease is determined. A wide range of other product attributes can also be tested, including, but are not limited to, oil content, protein content, starch content, product weight, test weight, product size, product color, and a variety of biochemical measurements that can be made on the product, such as amino acid levels, tocopherol levels, levels of various nutrients, micro-nutrients, vitamins, flavonoids, and other compounds. In some cases, the product may be tested for the yield of compounds resulting from introduced genetic material. Such genetic material may be endogenous to plant, or may be transgenic traits that have been introduced into the plant. Thereby, pollen donator strains can be identified that maximize the yield of transgenic gene products, such as pharmaceutical or nutraceutical products.

As discussed above, the present invention may be used with many types of crops, including, but not limited to, maize, wheat, rice, sorghum, oats, barley and other cereal crops. An advantage of the invention is that the product resulting from a single plant or less may be an experimental unit. If desired, product from multiple ovaries may be used. As discussed above, using product from a single plant, or less than a single plant, provides analytical advantages, as well as cost and resource advantages. The invention includes intentionally pollinating a designated female plant with pollen from at least one pollen donator strain. In many embodiments, the designated female plant will be pollinated with pollen from two or more pollen donator strains. Moreover, it is preferred that the designated females avoid self-pollination, although whether to allow self-pollination will depend on the particular trial being conducted. There are many ways to avoid self-pollination. As discussed above, a preferred method of the invention is to pollinate the female as soon as pollen receptors are available, but before pollen is being shed by the designated female plant. In some species and strains, this will occur naturally. In others,

TABLE 1

High Oil Topcross Comparison with the Method of the Invention

| System | Year | Plot Size | # Plots | # Strains Tested | Person-hours/strain | Land required Feet$^2$ |
|---|---|---|---|---|---|---|
| HOTC | 1 | 37 feet$^2$ | 4-6 | 3000 | 0.3 | 148-222 |
| Invention | 1 | 1 plant | 20 | 3000 | 0.2 | 29 |
| HOTC | 2 | 37 feet$^2$ | 8-10 | 600 | 0.6 | 296-370 |
| Invention | 2 | 1 plant | 60 | 600 | 0.4 | 87 |
| HOTC | 3 | 37 feet$^2$ | 12-15 | 60 | 1.2 | 444-555 |
| Invention | 3 | 1 plant | 180 | 60 | 0.8 | 261 |
| HOTC | 4 | 1,200 feet$^2$ | 20 | 6 | 20 | 24000 |
| Invention | 4 | 150 feet$^2$ | 20 | 6 | 5 | 3050 |

In the HOTC system, only one pollinator could be tested per plot, but the disclosed invention allows the testing of more pollinators per plot, such as ten or more different pollen donators. In addition, experimental variation would be greatly reduced due to an experimental unit consisting of manipulation of the flower may be required to allow pollination before self-pollination would otherwise occur, such as by mechanical, physical, or chemical means. Another option for avoiding self-pollination is by male sterility, including but not limited to, genetic male sterility, chemical male sterility, a treatment causing delayed male fertility, removal of the male components of the plant (for example, detasseling), and any other methods of male sterility known now or in the future.

The following example illustrates the present invention in more detail and is illustrative of how the invention described herein is implemented in corn.

Example 1

The invention described herein was practiced using three female corn varieties in one location in central Iowa in the summer of 2017. Under normal production conditions, these varieties will produce yellow kernels as a result of self-pollinations. The females as well as the pollen donators were grown in research plots at three different locations. The plants were grown in rows that had 30" spacing from neighboring rows and were approximately 17' in length. A mix of two different pollen donors (one producing white kernels and one producing purple kernels) that were unrelated to the yellow female corn variety were grown within these plots at a distance of more than 100 feet away from the female plants, and sometimes from a plot at a different location altogether. When the pollen donators were used as a male pollen source to pollinate, successful pollination of kernels was obvious to the naked eye by observing the color of the mature kernels on an ear. Yellow kernels were self-pollinations, while white or purple kernels were cross pollinations from the pollen mix.

To practice the invention, pollen from each pollen donator (white and purple) was bagged, maintaining identity, mixed at equal ratios and placed into overnight storage in a pollen bank. The following morning, the stored pollen was carried into the internal rows of the female corn production block. The mixture of pollen was manually applied to the females of at least 15 plants at the beginning of the normal pollination window in the morning. Each plant was marked with the pollen donators that were used to pollinate the plants within the row. The females that were pollinated were left to open pollinate so that pollen from the female could also compete with the pollen donor strain pollen that was carried into the plot. Yellow kernels that are on the ears at harvest can be assumed to be mostly, if not all, self-pollinations, while the white and purple kernels on these ears are the result of cross pollinations from the pollen donators. It is important to note that manual direction of the pollen was very precise and measured, and previous data generated by the inventors has indicated that plants in adjacent rows (and adjacent plants) exhibit few or no pollinations from the pollen that is directed to other plants. Plants that did not have the white and purple pollen directly applied to them had an average of 99% yellow kernels. These plants and resulting kernels served as controls to measure basal self-pollination percent in the block. Therefore, self-pollination frequency in the middle of this block of hybrids was very close to 100% under conventional methods of grain production and agrees with percent selfing in the middle of a grain production field (Bulant, C. and Gallais, A. (1998). *Crop Sci.* 38:1517-1525).

The results in Table 3 show that the invention is very effective at differentiating the effectiveness of each pollen donator with regard to its ability to increase cross-pollination kernel weight and test weight. Again, the ability to measure kernel weight and test weight from results on a single ear provided levels of statistical precision that are not achievable with current practices without utilizing thousands of plants.

TABLE 2

Grain Yield: Male Pollen Xenia Effect
Increase in Kernel Weight (%)

| Yellow Female | Pollen Mixture | Number of ears harvested | Male Source | |
|---|---|---|---|---|
| | | | Purple | White |
| AA | 1 | 39 | 2.4%* | 5.6%** |
| AA | 2 | 21 | 2.8%* | 7.0%** |
| BB | 3 | 11 | 4.0%* | 5.6%* |
| CC | 4 | 11 | −3.8%* | 0.0% |

*Significant at the 0.05 level
**Significant at the 0.01 level

In this example, the white pollen donors show an increase in kernel grain yield compared to the self-pollination in female AA and BB. The white pollen donor in pollen mixture 2 was the best pollinator for increasing grain yield within the AA female (p<0.01). In female CC, both the white and the purple pollen donator showed no increase in grain yield and both would be discarded in a breeding program. This demonstrates that the pollen mix will vary in its efficacy of increasing yield based on the genetics of both the female plant and the pollen mix. In general, the male source pollen results in an increase in yield that is statistically significantly higher than the standard yield. The white pollen donator, for example, may be advanced into further trials based on the 7% yield increase demonstrated on yellow female AA.

The efficiency gained in this type of a program compared to a normal commercial breeding and product advancement program is dramatic. The total plot size to evaluate each set of pollinators was approximately 15-30 square feet, with the range being based on the number of ears that were generated to test the pollinators. In a normal commercial testing program, this same testing would have taken 150-550 square feet during the very early stages of testing and more than 24,000 square feet in the later stages. In addition, this evaluation had very low coefficient of variation and had excellent statistical power to detect differences. In summary, this example illustrates how this invention could save more than 7 times the typical resources that would be required when using a conventional, commercial breeding program. In addition, this method reduces costs even further relative to a conventional breeding program (non-pollinator). Based on this analysis, and given a limited budget to spend on breeding, and given that the goal of any breeding program is to maximize gain from selection per dollar spent, shifting budgets away from conventional breeding and towards pollen donator breeding using this invention may prove beneficial.

Example 2

The invention described herein was practiced using two female corn varieties in one location in central Iowa in the summer of 2017. Under normal production conditions, this variety will produce white shriveled kernels as a result of self-pollinations. The plants were grown in rows that had 30" spacing from neighboring rows and were approximately 17' in length. A mix of three different pollen donors (one producing white non-shriveled kernels, one producing yellow non-shriveled kernels, and one producing purple non-shriveled kernels) that were unrelated to the yellow female corn varieties were grown at locations more than 100 feet away from the female plants, and sometimes from a plot at a different location altogether. When the pollen donators were used as a male pollen source to pollinate, successful pollination of kernels was obvious to the naked eye by observing the color of the mature kernels on an ear. White, shriveled kernels were self-pollinations, while white, purple or yellow starchy kernels were cross pollinations from the pollen mix.

To practice the invention, pollen from each pollen donor was bagged, maintaining identity, mixed at equal ratios and placed into overnight storage in a pollen bank. The following morning, the stored pollen was carried into the internal rows of the female corn production block. The mixture of pollen was manually applied to the females of at least 15 plants at the beginning of the normal pollination window in the morning. Each row was marked with the pollen donors that were used to pollinate the plants within the row. The females that were pollinated were left to open pollinate so that pollen from the female could also compete with the pollen donor strain pollen that was carried into the plot. White shriveled kernels that are on the ears at harvest can be assumed to be mostly, if not all, self-pollinations, while the white, purple and yellow non-shriveled kernels on these ears are the result of cross pollinations from the pollen donors. It is important to note that manual direction of the pollen was very precise and measured, and previous data generated by the inventors has indicated that plants in adjacent rows (and adjacent plants) exhibit few or no pollinations from the pollen that is directed to other plants. Plants that did not have the white, yellow and purple non-shriveled kernel producing pollen directly applied to them had an average of 99% white shriveled kernels. These plants and resulting kernels served as controls to measure basal self-pollination percent in the block. Therefore, self-pollination frequency in the middle of this block of hybrids was very close to 100% under conventional methods of grain production and agrees with percent selfing in the middle of a grain production field (Bulant, C. and Gallais, A. (1998). *Crop Sci.* 38:1517-1525).

The results in Table 3 show that the invention is very effective at differentiating the effectiveness of each pollen donor with regard to its ability to increase cross-pollination kernel weight and test weight in comparison to the self-pollination. Again, the ability to measure kernel weight and test weight from results on a single ear provided levels of statistical precision that are not achievable with current practices without utilizing thousands of plants. Note that in the following table, SP+SQ indicates combined data from both tested females.

TABLE 3

Percentage Increase in Kernel Weight Over Self Pollination

| White Female | Number of ears harvested | Male Pollen Donor Source | | |
|---|---|---|---|---|
| | | White | Yellow | Purple |
| SP | 11 | 31%** | 27%** | 28%** |
| SQ | 9 | 38%** | 26%** | 38%** |
| SP + SQ | 20 | 35%** | 26%** | 32%** |

**Significant at the 0.01 level

In this example, all pollinators showed a significantly greater kernel grain yield than the self-pollinations (p<0.01). Overall, the white pollen donor was the best pollinator for increasing grain yield within the SQ female. The purple pollen donor also showed the greatest increase in grain yield within the SQ female. The yellow pollen donor would be discarded in a breeding program. The purple pollen donor would also likely be discarded in a breeding program, depending on what selection intensity the breeder was using since, overall, the white pollen donor source shows the highest average yield increase. This is consistent with the anticipated result that the male source pollen resulted in an increase in yield that is statistically significantly higher than the standard yield, as a result of xenia combined with synchronous pollination.

The efficiency gained in this type of a program compared to a normal commercial breeding and product advancement program is dramatic. The total plot size to evaluate each set of pollen donors was approximately 15-30 square feet. In a normal commercial testing program, this same testing would have taken 150-550 square feet during the very early stages of testing and more than 24,000 square feet in the later stages. In addition, this evaluation had very low coefficient of variation and had excellent statistical power to detect differences. In summary, this example illustrates how this invention could save more than 7 times the typical resources that would be required when using a conventional, commercial program for pollen donor testing. As with the previous example, this method reduces costs relative to a conventional breeding program (non-pollinator).

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

What is claimed is:

1. A method of conducting a pollen donor strain trial on a single female plant to maximize at least one product attribute wherein experimental variation and variation caused from plant to plant comparisons is reduced or eliminated compared to trials with multiple female plants, comprising:

a) growing said single female plant;

b) pollinating said single female plant with pollen from a first male pollen donor strain wherein said pollen is intentionally applied manually or mechanically resulting in a first cross-pollinated product and pollen from a second male pollen donor strain wherein said pollen is intentionally applied manually or mechanically resulting in a second cross-pollinated product, wherein said first cross-pollinated product, said second cross-pollinated product, and a self-pollinated product have distinguishable phenotypes, c) growing the designated single female plant to maturity;

d) harvesting said products;

e) sorting said products from each other based on said distinguishable phenotypes; and f) comparing said at least one product attribute of said products.

2. The method of claim 1 wherein said single female plant is also pollinated with self-pollen.

3. The method of claim 1 wherein said single female plant is pollinated with pollen from 3, 4, 5, 6, 7, 8, 9, 10, 11, 12, 13, 14, 15, 16, 17, 18, 19, or 20 male pollen donator strains.

4. The method of claim 1 wherein the designated female plant is grown in specific challenging field conditions selected from the group consisting of:

a) high soil moisture;
b) low soil moisture;
c) high ambient temperature;
d) low ambient temperature;
e) low soil pH;
f) high soil pH;
g) short growing season;
h) long growing season;
i) low fertility;
j) high insect pressure; and
k) high disease pressure.

5. The method of claim 1 wherein at least one of said distinguishable phenotypes is caused by a genetic modification.

6. The method of claim 5 wherein at least one of said distinguishable phenotypes is caused by a transgene.

7. The method of claim 1 wherein said distinguishable phenotype is selected from the group consisting of seed color, seed color intensity, seed color pattern, seed shape, seed size, and combinations thereof.

8. The method of claim 1 wherein said plaint is maize and said distinguishable phenotype is selected from the group consisting of white endosperm, yellow endosperm, orange endosperm, opaque endosperm, non-opaque endosperm, purple plumule, non-purple plumule, colorless aleurone, purple aleurone, starch endosperm mutants, and combinations thereof.

9. The method of claim 1 wherein said distinguishable phenotype is selected form the group consisting of color marker genes, DsRed2, transgenes that increase anthocyanin, transgenes that alter cotyledon color, and combinations thereof.

10. The method of claim 1 wherein at least one of the male pollen donator are chosen for further breeding and product advancement.

11. The method of claim 1 wherein at least one of the male pollen donator are chosen for further breeding and product development based on said at least one product attribute.

12. The method of claim 1 wherein said plant is maize, wheat, rice, sorghum, oats, or barley.

* * * * *

UNITED STATES PATENT AND TRADEMARK OFFICE
CERTIFICATE OF CORRECTION

PATENT NO. : 10,993,390 B2
APPLICATION NO. : 15/934184
DATED : May 4, 2021
INVENTOR(S) : Todd Krone and Jason Cope Page 1 of 1

It is certified that error appears in the above-identified patent and that said Letters Patent is hereby corrected as shown below:

In the Claims

Claim 8, Column 16, Line 10, delete "plaint" and insert --plant-- therefor.

Claim 9, Column 16, Line 18, delete "form" and insert --from-- therefor.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*